United States Patent
Saccomanno

(10) Patent No.: US 6,773,584 B2
(45) Date of Patent: Aug. 10, 2004

(54) APPARATUS FOR DISINFECTING WATER USING ULTRAVIOLET RADIATION

(75) Inventor: Robert J. Saccomanno, Montville, NJ (US)

(73) Assignee: Honeywell International Inc., Morristown, NJ (US)

(*) Notice: Subject to any disclaimer, the term of this patent is extended or adjusted under 35 U.S.C. 154(b) by 1 day.

(21) Appl. No.: 10/268,567

(22) Filed: Oct. 9, 2002

(65) Prior Publication Data

US 2003/0089670 A1 May 15, 2003

Related U.S. Application Data

(60) Provisional application No. 60/330,174, filed on Oct. 17, 2001.

(51) Int. Cl.[7] .................................. C02F 1/32
(52) U.S. Cl. ................. 210/205; 96/224; 422/186.3
(58) Field of Search ............... 210/748, 198.1, 210/205; 96/224; 422/24, 186.3; 250/435

(56) References Cited

U.S. PATENT DOCUMENTS

| | | | |
|---|---|---|---|
| 3,182,193 A | 5/1965 | Ellner | |
| 4,482,809 A | 11/1984 | Maarschalkerweerd | |
| 5,069,782 A | 12/1991 | Moyher | |
| 5,393,419 A | 2/1995 | Tiede | |
| 5,413,768 A | 5/1995 | Stanley, Jr. | |
| 6,099,799 A | 8/2000 | Anderson | |
| 6,315,963 B1 * | 11/2001 | Speer | 422/186.3 |
| 6,447,721 B1 * | 9/2002 | Horton et al. | 422/24 |
| 6,552,351 B2 * | 4/2003 | Vitt | 250/435 |

FOREIGN PATENT DOCUMENTS

| | | |
|---|---|---|
| DE | 43 07 204 A | 9/1994 |
| JP | 10071189 A * | 3/1998 |
| WO | WO 99 52566 A | 10/1999 |
| WO | WO 01 60418 A | 8/2001 |

* cited by examiner

Primary Examiner—Frank M. Lawrence
(74) Attorney, Agent, or Firm—Kurt Luther; James W. Falk

(57) ABSTRACT

Ultraviolet radiation is used to disinfect water (5) in a flow tube, where the flow tube (10) acts a fluid filled light guide for the ultraviolet radiation and the ultraviolet radiation propagates through the flow tube via total internal reflection.

8 Claims, 3 Drawing Sheets

APPARATUS FOR DISINFECTING WATER USING ULTRAVIOLET RADIATION

BACKGROUND OF THE INVENTION

1. Technical Field

This invention relates to a water purification system using intense ultraviolet irradiation to break down chemical bonds in toxic compounds and to de-activate pathogens. The method can also be applied to any mass transport, including the purification of air. These systems can be applied to purify fluids containing naturally occurring toxins or those resulting from biological and chemical agents used in warfare.

2. Background Art

The first application of an ultra violet (UV) low-pressure mercury vapor discharge lamp to disinfect water was in Marseilles, France in 1901. However, it was not until 1955 that UV disinfection became widely applied in Europe for potable water. In that year UV disinfection equipment was installed in Switzerland, Austria and Norway. Following the discovery of the formation of halogenated hydrocarbons during chlorination, UV disinfection since became popular in most European countries.

U.S. Pat. No. 1,196,481, issued Aug. 29, 1916 described the use of a mercury vapor lamp to generate sufficient ultraviolet light (mostly 254-nm wavelength) to purify water. This basic approach, built upon the UV efficacy of extended-arc continuous-duty mercury based lamps, has been refined over the years, such as in Ellner U.S. Pat. No. 3,182,193 issued May 4, 1965, Maarschalkerweerd U.S. Pat. No. 4,482,809 issued Nov. 13, 1984, Moyher U.S. Pat. No. 5,069,782 issued Dec. 3, 1991, Tiede U.S. Pat. No. 5,393,419 issued Feb. 28, 1995, and Anderson U.S. Pat. No. 6,099,799 issued Aug. 8, 2000. Much of the latter art improved upon aspects related to commercial viability, such as improving UV dosage uniformity through the use of baffles, UV-transparent coils, and controlled turbulence; increasing UV intensity for higher flow rates by increasing the number of lamps in a given volume; and improving maintenance through the use of Teflon coatings, wiper mechanisms, and adding turbulence.

Prior art UV water disinfecting systems expose the water to UV radiation such that the radiation passes through the water, strikes a reflecting surface and then passes through the water after reflection. The reflecting surfaces absorb a significant amount of radiation. There is a long-felt need to improve the efficiency of such systems.

SUMMARY OF THE INVENTION

My invention is an apparatus and method for disinfecting water, or other fluid, that channels water through one end of a tube and couples ultraviolet (UV) energy from a high intensity lamp through the tube from the other end. The water, or other fluid, acts like the core of a liquid light pipe, with an air gap surrounding the tube acting as a low index cladding. The tube itself is constructed of a non-UV-absorbing material, such as UV-grade fused silica glass. Advantageously, the use of light-pipe technology, which is based on total internal reflection (TIR), ensures that all the input UV radiation is dissipated in the water. Preferably, the tube is polygonal in cross-section, which is known in the art to maximize light flux uniformity within a light pipe.

Embodiments of my invention with multiple zones efficiently handle a wide range of water absorption coefficients, all at the highest practical efficiency. In accordance with an aspect of my invention one of three zones is defined by a concentric UV-grade tubing concentrically around only a portion of the tube through which the water flows and others of these zones are defined between these tubes and the enclosing outer tube.

BRIEF DESCRIPTION OF DRAWINGS

Figure 1:
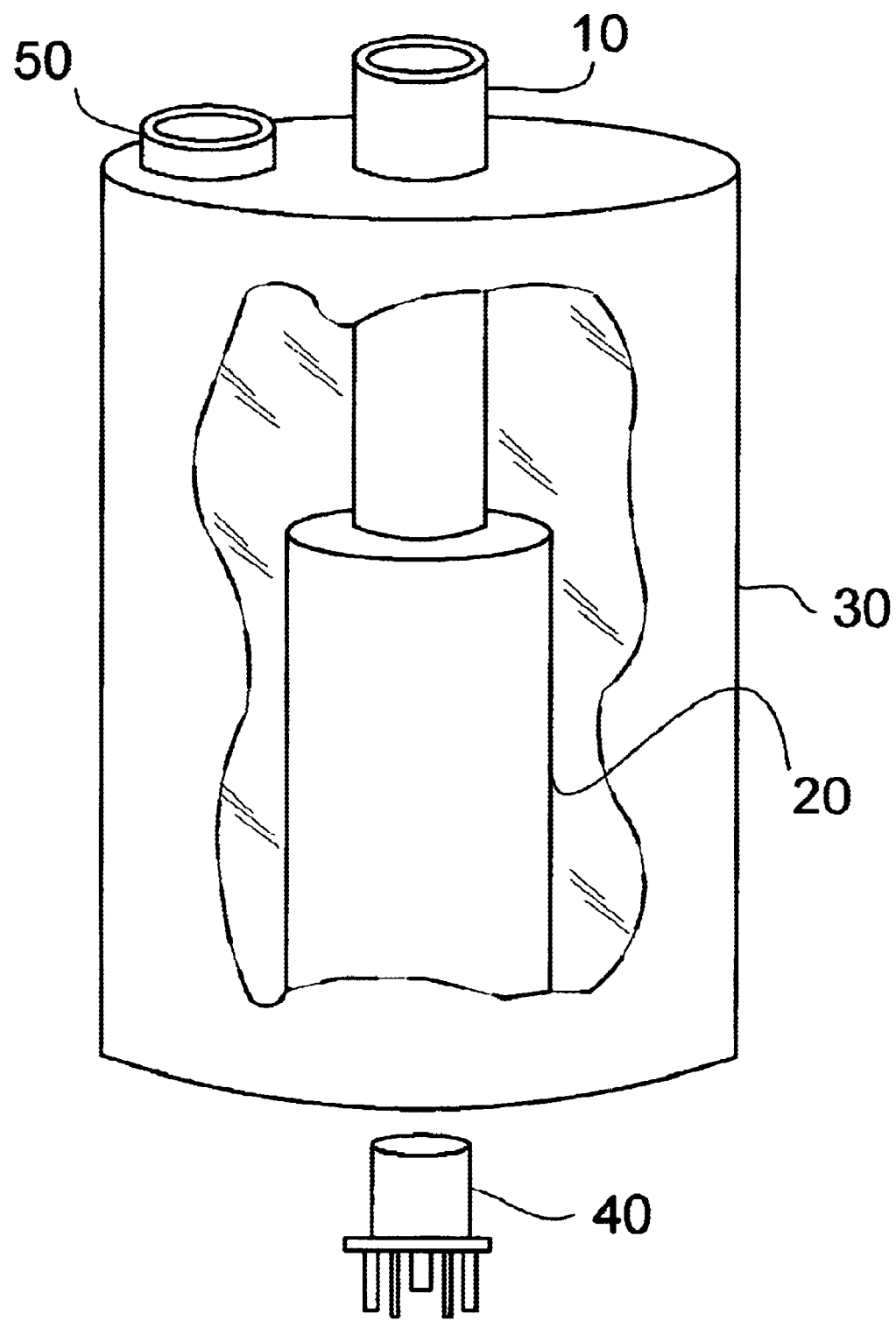

Brief Description of the Several Views of the Drawing

FIG. 1 depicts an apparatus for disinfecting water using ultraviolet radiation (UV) in accordance with one illustrative embodiment of my invention.

Figure 2:
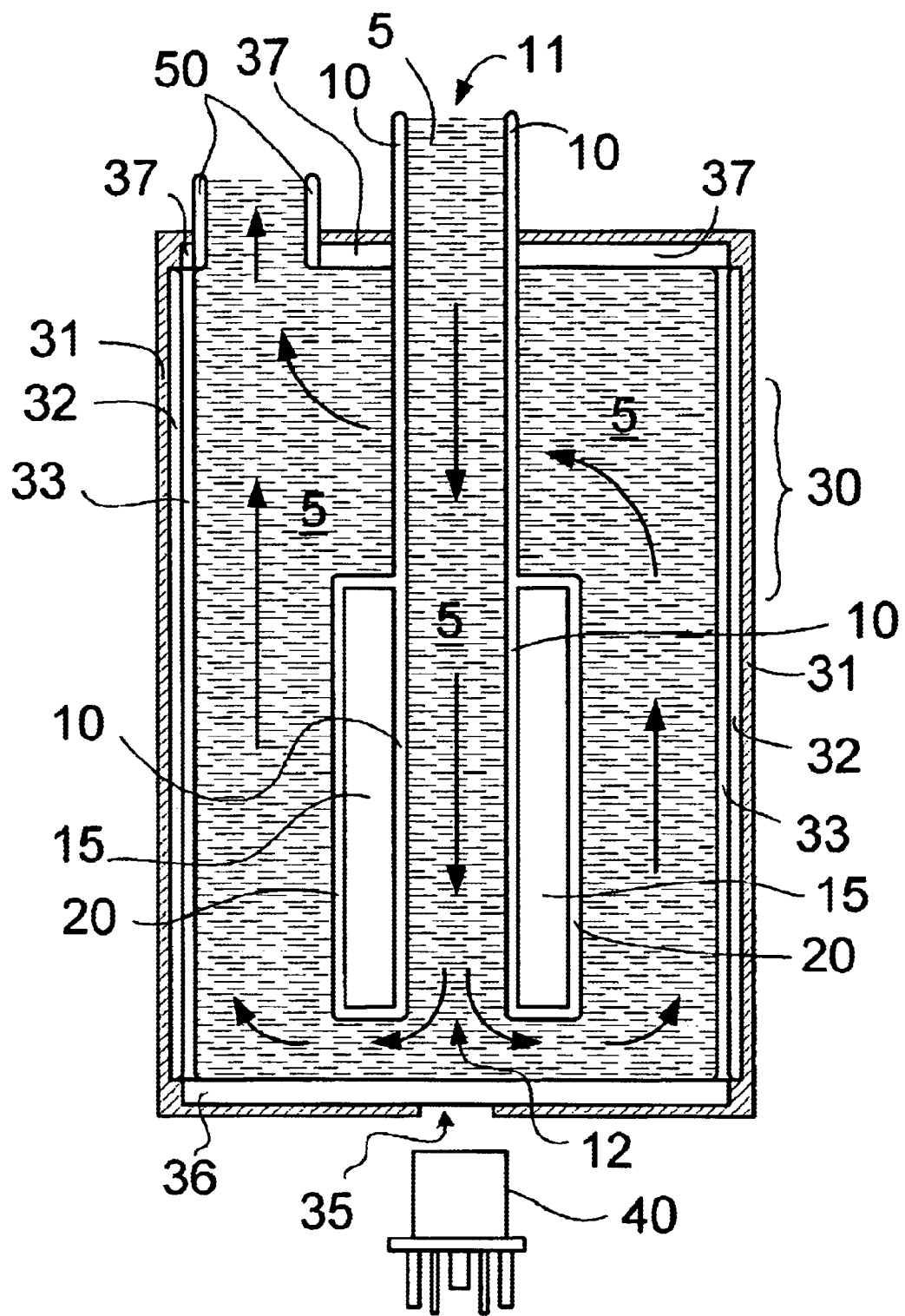

FIG. 2 depicts a sectional view of the UV disinfecting apparatus of FIG. 1.

Figure 3:
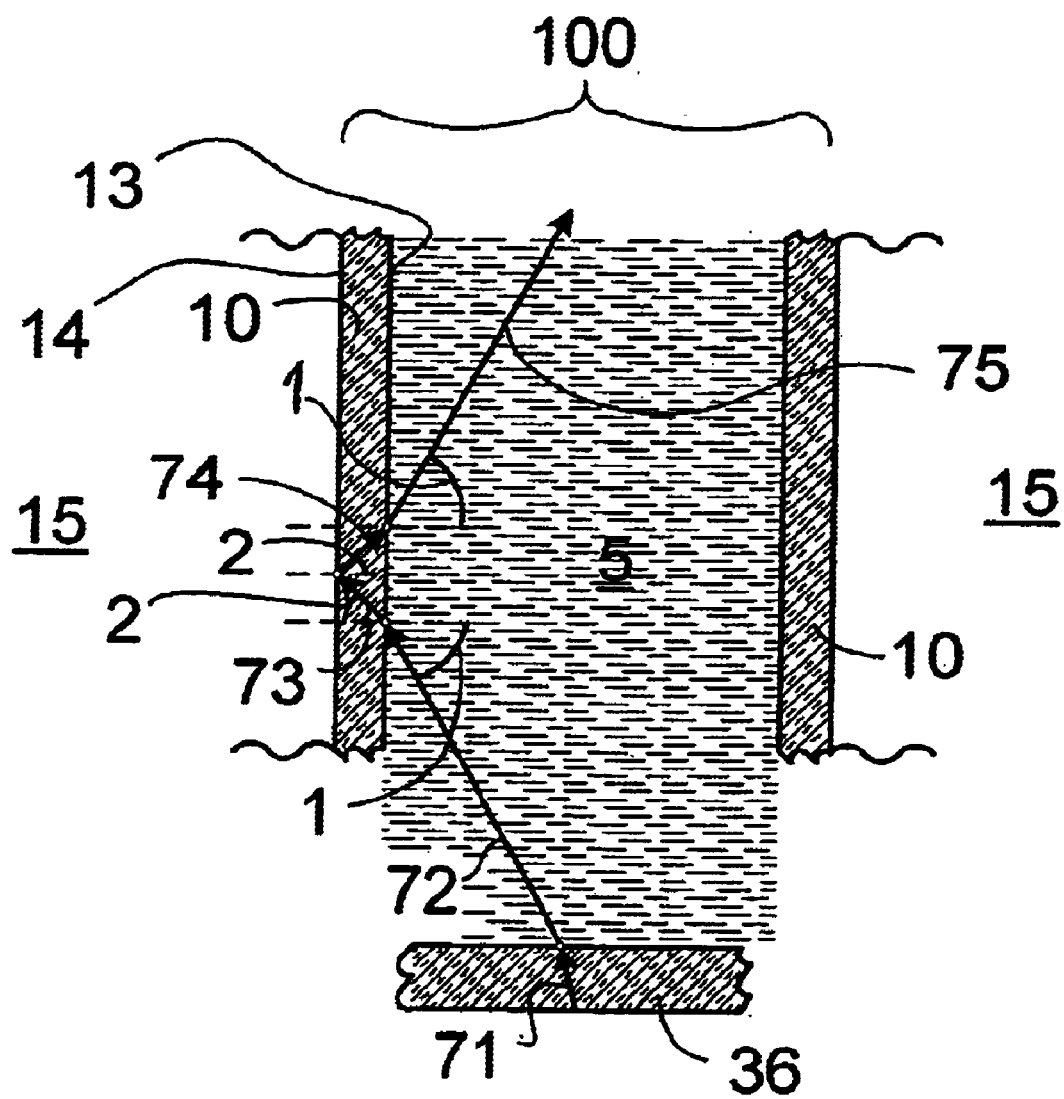

FIG. 3 depicts a light pipe irradiation zone within the UV disinfecting apparatus of FIG. 1, showing how the ultraviolet radiation is contained using total internal reflection (TIR).

List of Reference Numbers for the Major Elements in the Drawing

The following is a list of the major elements in the drawings in numerical order.

5 fluid (to be disinfected)
 10 fluid inlet tube
 11 entrance end (fluid inlet tube)
 12 exit end (fluid inlet tube)
 13 internal surface (fluid inlet tube)
 14 external surface (fluid inlet tube)
 15 concentric gap (between inlet tube and optical cladding tube)
 20 optical cladding tube
 30 fluid containment vessel
 31 ultraviolet mirror (fluid containment vessel internal surface)
 32 air gap (fluid containment vessel)
 33 inner tube (of fluid containment vessel)
 35 ultraviolet inlet aperture
 36 lower ultraviolet window surface
 37 upper ultraviolet window surface
 40 high intensity ultraviolet lamp
 50 fluid outlet tube
 71 first UV light ray (exiting lower ultraviolet window surface)
 72 second UV light ray (exiting fluid)
 73 third UV light ray (entering fluid inlet tube internal surface)
 74 fourth UV light ray (exiting fluid inlet tube internal surface)
 75 fifth UV light ray (entering fluid)
 100 light pipe (formed from fluid, fluid inlet tube, and concentric gap)
 1 incidence angle (refraction at fluid inlet tube internal surface)
 2 internal reflection angle (reflection at fluid inlet tube external surface)

DESCRIPTION OF THE INVENTION

Mode(s) for Carrying Out the Invention

Referring first to FIG. 1, the basic construction of an ultraviolet (UV) water disinfecting device in accordance with my invention is shown, including a fluid inlet tube 10 that acts as a central light pipe, an optical cladding tube 20 around the lower portion of fluid inlet tube 10 and defining therewith a concentric gap 15, a fluid containment vessel 30, a fluid outlet tube 50, and a high intensity UV lamp 40, such as a flashlamp.

Referring next to FIG. 2, the fluid containment vessel 30 includes an internal surface configured as an ultraviolet mirror 31; for example, the fluid containment vessel may be constructed from aluminum and the internal surface may be polished aluminum. A fluid 5 to be disinfected, such as water, enters the fluid inlet tube 10 through an entrance end 11. The fluid inlet tube 10 may be manufactured, for example from UV-grade fused silica.

The fluid 5 travels through the fluid inlet tube 10 towards the high intensity UV lamp 40 and exits the fluid inlet tube 10 at the exit end 12. The fluid 5 flow then strikes an ultraviolet (UV) window lower surface 36, which forms a portion of the lower end of fluid containment vessel 30. Next, the fluid 5 flow is redirected to the fluid outlet tube 50, which is located in the upper end of the fluid containment vessel 30.

The fluid 5 is contained within the fluid containment vessel 30. The fluid containment vessel 30 includes an inner tube 33, which may be constructed from UV-grade fused silica, contained within an outer aluminum shell with a reflective interior surface defining a UV mirror 31, with an air gap 32 between the outer shell and the inner tube 33. Then ends of the outer tube 30 are closed off with the lower ultraviolet window surface 36 and an ultraviolet window upper surface 37.

The preferred orientation of the ultraviolet (UV) water disinfecting device is vertical, so that the fluid 5 flow approximates plug-flow, and the position of the fluid outlet tube 50 is at or near the highest point, allowing for quick and efficient removal of undesirable air bubbles. Air bubbles present in the fluid 5 can form scattering sites for the UV radiation thereby degrading system efficiency. These UV scattering sites result in UV radiation being directed at less than optimum angles causing reflections from the fluid containment vessel internal surface, the ultraviolet mirror 31 that is approximately 86% reflective when composed of aluminum tube. Without these UV scattering sites, the ultraviolet radiation is dissipated mostly within the fluid 5, because all reflections are near loss-less because of the total internal reflection (TIR) operation of a light pipe.

Referring next to FIG. 3, a light pipe 100 region is formed from the fluid 5, such as water, the fluid inlet tube 10, such as a UV-grade fused silica tube, and the concentric gap 15, such as an air gap or a vacuum gap. The concentric gap 15 is hydraulically isolated from the fluid 5, in order to allow the light pipe 100 to operate. Light pipe operation is based on the refractive index of the concentric gap being less than the refractive index of the fluid 5. The refractive indices of fused silica and water in the UV region of the light spectrum are shown in Table 1 below.

TABLE 1

Refractive Indices of Fused Silica and Water

| Wavelength (nm) | Refractive Index |
|---|---|
| Fused Silica UV Grade (SiO2) | |
| 170 | 1.615 |
| 185 | 1.575 |
| 200 | 1.550 |
| 214 | 1.534 |
| 280 | 1.494 |
| 302 | 1.487 |
| 436 | 1.467 |
| 546 | 1.460 |
| 656 | 1.456 |
| Water | |
| 172 | 1.568 |
| 185 | 1.549 |
| 200 | 1.543 |
| 215 | 1.513 |
| 280 | 1.492 |
| 305 | 1.475 |
| 450 | 1.344 |
| 550 | 1.336 |
| 650 | 1.331 |

As shown in Table 1, water has about the same refractive index as UV grade Silica glass in the ultraviolet (UV) portion of the light spectrum.

Ultraviolet (UV) radiation is transmitted from the high intensity ultraviolet lamp 40, passes through the ultraviolet inlet aperture 35, and enters the lower ultraviolet window surface 36 as shown in FIG. 2. A first UV light ray 71 exits lower ultraviolet window surface, is bent by refraction, and enters the fluid 5, defining a second UV light ray 72. The second UV light ray 72 impinges upon the internal surface 13 of the fluid inlet tube 10, which is in contact with the fluid 5, at an incidence angle 1, where incidence angle 1 is measured with reference to the surface normal of internal surface 13. As the second UV light ray 72 enters a sidewall of the fluid inlet tube 10, it is bent by refraction and redirected at a new internal reflection angle 2, defining a third UV light ray 73.

The value of angle 2 is a function of incident angle 1 and the refractive indices of the fluid 5 and the material, such as UV-grade silica, from which the fluid inlet tube 10 is constructed. The third UV light ray 73 continues through the fluid inlet tube 10 material and impinges upon the external surface 14 of the fluid inlet tube that is in contact with the concentric gap 15. The third UV light ray 73 is reflected back into the sidewall of the fluid inlet tube 10, defining a fourth UV light ray 74 when the refractive indices of the fluid inlet tube 10 material and the concentric gap 15 meet certain conditions as defined by Snell's Law. The refractive index of the concentric gap 15 is defined by the material contained in the concentric gap such as glass, plexiglas, or acrylic, or by the refractive index of a vacuum if no material is contained within the concentric gap 15.

It is a feature of my invention that a light pipe 100 region exists for at least part of the length of the fluid inlet tube 10. Therefore, it is required that the incidence angle 2 be limited to a predetermined range in accordance with the refractive indices of the fluid 5, the material from which the fluid inlet tube 10 is constructed, and the concentric gap 15. In a preferred embodiment of my invention, the fluid inlet tube 10 is constructed from UV-grade silica glass, the fluid 5 to be disinfected is water, and the concentric gap 15 contains a vacuum.

Alternate Embodiments

Alternate embodiments may be devised without departing from the spirit or the scope of the invention. For example, the methods described herein can be applied not only to water flow, but also to other fluids that require purification such as breathable air.

What is claimed is:

1. A system to disinfect water using ultraviolet radiation (UV), said system comprising:

(a) a fluid inlet tube (10), for carrying a fluid (5) to be disinfected, said fluid having a first refractive index, said fluid inlet tube constructed from a material having a second refractive index and comprising an entrance end (11), a distally opposing exit end (12), an internal surface (13) in contact with said fluid, and an external surface (14);

(b) an optical cladding tube (20) disposed around the external surface of the fluid inlet tube defining a concentric gap (15) between said fluid inlet tube and said optical cladding tube, wherein said concentric gap has a third refractive index;

(c) a fluid containment vessel (30) around said fluid inlet tube and said optical cladding tube wherein a portion of said fluid inlet tube extends from said fluid containment vessel and said concentric gap is hydraulically isolated from said fluid containment vessel;

(d) an ultraviolet inlet aperture (35) disposed on and forming a portion of said fluid containment vessel;

(e) a high intensity ultraviolet lamp (40) providing ultraviolet radiation that passes through said ultraviolet inlet aperture and impinges upon said internal surface of said fluid inlet tube at a predetermined range of incidence angles;

(i) wherein said predetermined range of incidence angles is limited in accordance with said first, second and third refractive indices such that the inlet tube acts as a light pipe wherein substantially all of the ultraviolet radiation is propagated through said inlet tube via total internal reflection; and (f) a fluid outlet tube (50) extending from said fluid containment vessel.

2. The system of claim 1 wherein the concentric gap contains a vacuum.

3. The system of claim 1 wherein the concentric gap contains a gas selected from the group consisting of: dry air, nitrogen, and argon.

4. The system of claim 1 wherein the concentric gap contains a clear solid selected from the group consisting of: glass, and acrylic.

5. The system of claim 1 wherein said fluid to be disinfected is potable water.

6. The system of claim 1 wherein said fluid to be disinfected is breathable air.

7. The system of claim 1 wherein said fluid inlet tube and said optical cladding tube each have a polygonal cross-section.

8. The system of claim 1 wherein a portion of said fluid inlet tube located within said fluid containment vessel extends past an end of said optical cladding tube.

* * * * *

UNITED STATES PATENT AND TRADEMARK OFFICE
CERTIFICATE OF CORRECTION

| | |
|---|---|
| PATENT NO. | : 6,773,584 B2 |
| APPLICATION NO. | : 10/268567 |
| DATED | : August 10, 2004 |
| INVENTOR(S) | : Robert J. Saccomanno |

It is certified that error appears in the above-identified patent and that said Letters Patent is hereby corrected as shown below:

At column 3, line 57, replace "1.549" with -- 1.492 --.

At column 3, line 59, replace "1.543" with -- 1.452 --.

At column 3, line 60, replace "1.513" with -- 1.427 --.

At column 3, line 61, replace "1,492" with -- 1.379 --.

At column 3, line 62, replace "1.475" with -- 1.370 --.

AS column 3, line 65, replace " about the same" with -- a lower --.

At column 3, line 66, replace "as" with -- than ---.

Signed and Sealed this

Fifteenth Day of August, 2006

JON W. DUDAS
*Director of the United States Patent and Trademark Office*